United States Patent
Walker et al.

(10) Patent No.: US 10,239,857 B2
(45) Date of Patent: Mar. 26, 2019

(54) PROCESSES FOR THE PREPARATION OF 2-THIOPHENECARBONYL CHLORIDE

(71) Applicant: Monsanto Technology LLC, St. Louis, MO (US)

(72) Inventors: Daniel P. Walker, St. Charles, MO (US); William H. Miller, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 15/563,008

(22) PCT Filed: Mar. 31, 2016

(86) PCT No.: PCT/US2016/025159
§ 371 (c)(1),
(2) Date: Sep. 29, 2017

(87) PCT Pub. No.: WO2016/161063
PCT Pub. Date: Oct. 6, 2016

(65) Prior Publication Data
US 2018/0162830 A1    Jun. 14, 2018

Related U.S. Application Data

(60) Provisional application No. 62/140,915, filed on Mar. 31, 2015.

(51) Int. Cl.
*C07D 271/06*    (2006.01)
*C07D 333/38*    (2006.01)
*C07D 333/22*    (2006.01)
*C07D 333/12*    (2006.01)

(52) U.S. Cl.
CPC ......... *C07D 333/38* (2013.01); *C07D 271/06* (2013.01); *C07D 333/12* (2013.01); *C07D 333/22* (2013.01)

(58) Field of Classification Search
CPC .. C07D 271/06; C07D 333/40; C07D 333/12; C07D 333/22; C07D 333/38
USPC .......................................................... 549/72
See application file for complete search history.

(56) References Cited

U.S. PATENT DOCUMENTS

| 2,229,897 | A |  | 1/1941 | Migrdichian |  |
|---|---|---|---|---|---|
| 3,741,984 | A |  | 6/1973 | Sheeran |  |
| 3,959,569 | A |  | 5/1976 | Burkholder, Jr. |  |
| 4,556,672 | A | * | 12/1985 | Kadin | C07D 209/34 514/255.05 |
| 5,534,541 | A |  | 7/1996 | Drauz et al. |  |
| 8,435,999 | B2 | * | 5/2013 | Williams | A01N 43/76 514/255.05 |
| 9,040,711 | B2 | * | 5/2015 | Miller | C07D 271/06 548/131 |
| 9,273,037 | B2 | * | 3/2016 | Miller | C07D 271/06 |
| 2008/0167286 | A1 | * | 7/2008 | Gopalakrishnan | A61K 31/4245 514/210.16 |
| 2011/0112311 | A1 | * | 5/2011 | Ando | C07D 333/40 549/71 |
| 2014/0039197 | A1 |  | 2/2014 | Miller et al. |  |

FOREIGN PATENT DOCUMENTS

CN            103980265 A          3/2014

OTHER PUBLICATIONS

Jones, L.W., et al., "Rearrangements of Some New Hydroxamic Acids Related to Heterocyclic Acids and to Diphenyl- and Triphenyl-Acetic Acids." 1921, JACS, 43/11:2422-2448, 27 pages.
Dhar, P., et al., "Synthesis, Antimicrobial Evaluation, and Structure—Activity Relationship of α-Pinene Derivatives," 2014, J Agric Food Chem, 62:3548-3552, 5 pages.
Graf, R., "Umsetzungen Mit Olefinen und Aldehyden; Uber B-Lactame," 1963, Liebigs Ann Chem Bd, 661:111-161, 47 pages.
Gronowitz, S., et al., "Some Substitution Reactions of 2-(2'-Thienyl)pyrimidine and 2-(3'-Thienyl)pyrimidine," 1977, Acta Chemica Scandinavica, B, 31:771-780, 10 pages.
Jones, L.W., et al., "Rearrangements of Some New Hydroxamic Acids Related to Heterocyclic Acids and to Diphenyl- and Triphenyl-Acetic Acids." 1921, JACS, 43/11:2422-2448, p. 2422 only, 1 page.
Maksay, G., et al., "Synthesis of Heteroaromatic Tropeines and Heterogeneous Binding to Glycine Receptors," 2009, Bioorg Med Chem, 17/19:6872-6878, Abstract Only, 1 page.
Vebrel, J., et al., "Synthese de methoxycarbonylindenes, dihydro-1,2 napthalenese et benzocycloheptene. Obtention des indanone-1, des tetralones-1 et de la benzosuberone correspondantes," 1982, Bulletin de la Societe Chimique de France, 34:II-116-II-124, 9 pages.
Vorbruggen, H., et al., "The Introduction of Nitrile-Groups into Heterocycles and Conversion of Carboxylic Groups into their Corresponding Nitriles with Chlorosulfonylisocyanate and Triethylamine," 1994, Tetrahedron, 50/22:6549-6558, 10 pages.
International Search Report and Written Opinion issued in PCT/US2016/25159, dated Jun. 13, 2016, 11 pages.

* cited by examiner

*Primary Examiner* — Nyeemah A Grazier
(74) *Attorney, Agent, or Firm* — Stinson Leonard Street LLP; Lawrence M. Lavin, Jr.

(57) ABSTRACT

Provided herein are processes for the preparation of 2-thiophenecarbonyl chloride, which is useful, for example, in the preparation of 3,5-disubstituted-1,2,4-oxadiazoles, such as tioxazafen (3-phenyl-5-(2-thienyl)-1,2,4-oxadiazole).

19 Claims, No Drawings

PROCESSES FOR THE PREPARATION OF 2-THIOPHENECARBONYL CHLORIDE

REFERENCE TO RELATED APPLICATIONS

This application is the 371 National Stage Application of International Application Serial No. PCT/US2016/025159, filed Mar. 31, 2016, and claims the benefit of U.S. Provisional Application Ser. No. 62/140,915, filed Mar. 31, 2015, the contents of which are herein incorporated by reference.

FIELD

Provided herein are processes for the preparation of 2-thiophenecarbonyl chloride.

BACKGROUND

Acyl chlorides are useful as starting materials and reagents in the preparation of a wide variety of industrially useful compounds. For example, U.S. Pub. No. 2014/0039197 A1 reports that acyl chlorides can be reacted with N-hydroxyamidines in the preparation of 3,5-disubstituted-1,2,4-oxadiazoles, which are useful for, in part, nematode control in agriculture. For example, 2-thiophenecarbonyl chloride is useful in the preparation of tioxazafen (3-phenyl-5-(2-thienyl)-1,2,4-oxadiazole) by reaction with benzamide oxime.

While methods for preparing 2-thiophenecarbonyl chloride are known in the art, alternative routes that may result in a more efficient synthesis are highly desirable.

Citation of any reference above is not to be construed as an admission that such reference is prior art to the present application.

SUMMARY

Provided herein are processes for the preparation of 2-thiophenecarbonyl chloride.

For example, in one embodiment, the process comprises reacting thiophene with chlorosulfonyl isocyanate in a reaction medium comprising an organic solvent, thereby producing (thiophene-2-carbonyl)sulfamoyl chloride, wherein the reaction is initiated by mixing the thiophene and the chlorosulfonyl isocyanate, and wherein the chlorosulfonyl isocyanate is present in molar excess relative to thiophene.

In another embodiment, the process comprises reacting thiophene with chlorosulfonyl isocyanate in a reaction medium comprising an organic solvent, thereby producing (thiophene-2-carbonyl)sulfamoyl chloride, wherein the organic solvent comprises dibutyl ether.

In a further embodiment, the process comprises mixing a first liquid medium comprising thiophene dissolved in dibutyl ether and a second liquid medium comprising chlorosulfonyl isocyanate, thereby producing a third liquid medium comprising (thiophene-2-carbonyl)sulfamoyl chloride in the form of a substantially homogeneous solution or a solid suspension in a liquid organic phase comprising dibutyl ether, wherein the chlorosulfonyl isocyanate is present in the second liquid medium in molar excess relative to thiophene in the first liquid medium; adding at least a portion of the third liquid medium to an aqueous medium comprising hydrochloric acid or sulfuric acid, thereby producing a fourth liquid medium comprising 2-thiophenecarboxylic acid dissolved in an organic phase comprising dibutyl ether; and reacting at least a portion of the 2-thiophenecarboxylic acid present in the fourth liquid medium with thionyl chloride, thereby producing a reaction medium comprising 2-thiophenecarbonyl chloride.

In a further embodiment, the process comprises mixing a first liquid medium comprising thiophene dissolved in dibutyl ether and a second liquid medium comprising chlorosulfonyl isocyanate, thereby producing a third liquid medium comprising (thiophene-2-carbonyl)sulfamoyl chloride in the form of a substantially homogeneous solution or a solid suspension in a liquid organic phase comprising dibutyl ether, wherein the chlorosulfonyl isocyanate is present in the second liquid medium in molar excess relative to thiophene in the first liquid medium; adding at least a portion of the third liquid medium to an aqueous medium comprising sodium hydroxide or potassium hydroxide, thereby producing a fourth liquid medium comprising a salt form of 2-thiophenecarboxylic acid in an organic phase comprising dibutyl ether; neutralizing at least a portion of the fourth liquid medium to a fifth liquid medium comprising 2-thiophenecarboxylic acid dissolved in an organic phase comprising dibutyl ether; and reacting at least a portion of the 2-thiophenecarboxylic acid present in the fifth liquid medium with thionyl chloride, thereby producing a reaction medium comprising 2-thiophenecarbonyl chloride.

In a further embodiment, the process comprises mixing a first liquid medium comprising thiophene dissolved in dibutyl ether and a second liquid medium comprising chlorosulfonyl isocyanate, thereby producing a third liquid medium comprising (thiophene-2-carbonyl)sulfamoyl chloride in the form of a substantially homogeneous solution or a solid suspension in a liquid organic phase comprising dibutyl ether, wherein the chlorosulfonyl isocyanate is present in the second liquid medium in molar excess relative to thiophene in the first liquid medium; adding at least a portion of the third liquid medium to an aqueous medium comprising water, thereby producing a fourth liquid medium comprising 2-thiophenecarboxamide; contacting at least a portion of the forth liquid medium in the presence of a strong acid or a strong base, thereby producing a fifth liquid medium of 2-thiophenecarboxylic acid in an organic phase comprising dibutyl ether; and reacting at least a portion of the 2-thiophenecarboxylic acid present in the fifth liquid medium with thionyl chloride, thereby producing a reaction medium comprising 2-thiophenecarbonyl chloride.

In a further embodiment, the process is directed to the preparation of a 3,5-disubstituted 1,2,4-oxadiazole of Formula (I) or a salt thereof,

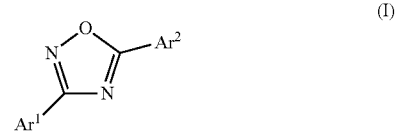

(I)

and comprises adding a first liquid medium comprising thiophene dissolved in dibutyl ether to a second liquid medium comprising chlorosulfonyl isocyanate, thereby producing a third liquid medium comprising (thiophene-2-carbonyl)sulfamoyl chloride in the form of a substantially homogeneous solution or a solid suspension in a liquid organic phase comprising dibutyl ether, wherein the chlorosulfonyl isocyanate is present in the second liquid medium in molar excess relative to thiophene in the first liquid medium; adding at least a portion of the third liquid medium to an aqueous medium comprising a strong acid or a strong base, thereby producing a fourth liquid medium comprising 2-thiophenecarboxylic acid dissolved in an organic phase comprising dibutyl ether; reacting at least a portion of the 2-thiophenecarboxylic acid present in the fourth liquid medium with thionyl chloride, thereby producing a reaction medium comprising 2-thiophenecarbonyl chloride; and reacting at least a portion of the 2-thiophenecarbonyl chloride obtained in the fourth liquid reaction medium with an N-hydroxyamidine of Formula (II), or a tautomeric form thereof,

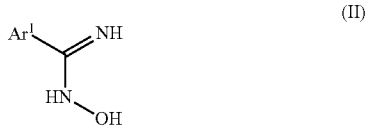
(II)

wherein $Ar^1$ is selected from the group consisting of phenyl, pyridyl, pyrazyl, oxazolyl or isoxazolyl, each of which can be optionally independently substituted with one or more substituents selected from the group consisting of halogen, $CF_3$, $CH_3$, $OCF_3$, $OCH_3$, CN and C(H)O, and $Ar^2$ is thienyl, which can be optionally independently substituted with one or more substituents selected from the group consisting of fluorine, chlorine, $CH_3$, and $OCF_3$.

DETAILED DESCRIPTION

Generally, the present disclosure is directed to improved processes for the preparation of 2-thiophenecarbonyl chloride.

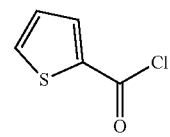

2-thiophenecarbonyl chloride
(TCC)

Various embodiments of the process enable greater ease of production, milder reaction conditions, reduced reaction time cycles, fewer reaction intermediates, and/or significantly reduced capital equipment requirements.

Solvents

Each of the process steps described herein in the preparation 2-thiophenecarbonyl chloride may be conducted in a reaction medium comprising an organic solvent. Solvents used to form the reaction medium may be selected on the basis of one or more criteria to facilitate simplification and overall economics of the process. In general, the process steps described herein can be conducted utilizing batch, semibatch, or continuous reactor designs.

As disclosed herein, in one embodiment, the solvent may be selected so that each of the process steps can be carried out in a reaction medium comprising the selected solvent. The use of a single-solvent synthesis process provides a number of significant benefits. Processes with fewer isolation steps and/or solvents typically are more efficient, are less expensive to operate, and can significantly reduce capital equipment expenditures required for large scale manufacturing operations. In one embodiment of the process described herein, a particular advantage is that it is not necessary to isolate the product of each reaction step for use in a subsequent step—the entire organic solvent phase can be transferred from one step to the next without need for purification or isolation of the intermediate reaction products. This can be particularly advantageous in the case of hydrolytically unstable intermediates. In other embodiments, the solvent in the reaction medium may be exchanged between one or more of the process steps, wherein suitable solvents are selected independently from each other.

In one embodiment, the organic solvent may form an azeotrope with water. The formation of an azeotrope facilitates removal, via e.g. evaporation or distillation, of the water in the 2-thiophenecarboxylic acid intermediate to substantially anhydrous conditions for effective use of the chlorinating reagent during subsequent conversion to the 2-thiophenecarbonyl chloride product.

In various embodiments, the solvent exhibits a boiling point that facilitates separation of the solvent from the 2-thiophenecarbonyl chloride product during distillation; does not exhibit significant reactivity in the presence of any reagent, intermediate species or byproducts described herein; or is stable in the presence of strong acids used in the hydrolysis step described herein.

Non-limiting examples of organic solvents suitable for use in connection with the process described herein include $C_1$-$C_{10}$ alkane solvents, $C_1$-$C_{10}$ halogenated alkane solvents, $C_1$-$C_{10}$ alkylbenzenes, halogenated aromatic solvents, dialkyl ether solvents of the general formula R—O—R', wherein R and R' are each independently selected from $C_1$-$C_6$ alkyl, and ester solvents of the formula R—C(O)O—R' wherein R and R' are each independently selected from $C_1$-$C_6$ alkyl.

In some embodiments, the organic solvent comprises a $C_1$-$C_{10}$ alkane compound. The compound may comprise one or more $C_1$-$C_{10}$ linear, branched or cyclic alkyl groups. By way of non-limiting example, the organic solvent may comprise hexane, 2-methylhexane, or cyclohexane.

In some embodiments, the organic solvent comprises a $C_1$-$C_{10}$ halogenated alkane solvent. The compound may comprise one or more $C_1$-$C_{10}$ linear, branched or cyclic alkyl groups. In some embodiments, the compound may comprise one or more halogen substituents independently selected from F, Cl, and Br. For example, the compound may comprise from one to six halogen substituents. By way of non-limiting example, the organic solvent may comprise dichloromethane, dichloroethane, chloroform, or carbon tetrachloride.

In some embodiments, the organic solvent comprises a $C_1$-$C_{10}$ alkylbenzene compound. The compound may comprise one or more $C_1$-$C_{10}$ linear, branched or cyclic alkyl groups, each of which may be optionally independently substituted with one or more halogen substituents independently selected from F, Cl, and Br. For example, the compound may comprise from one to six halogen substituents. In some embodiments, the alkyl groups are saturated alkyl groups. By way of non-limiting example, the organic solvent may comprise toluene, o-xylene, p-xylene, m-xylene, xylenes, trimethylbenzene, or trifluorotoluene.

In some embodiments, the organic solvent comprises a halogenated aromatic compound comprising one or more halogen substituents independently selected from F, Cl, and Br. For example, the compound may comprise from one to six halogen substituents. By way of non-limiting example, the organic solvent may comprise chlorobenzene, dichlorobenzene, chlorotoluene, or hexafluorobenzene.

In some embodiments, the organic solvent comprises a compound of the formula R—O—R' wherein R is selected from $C_4$-$C_6$ cycloalkyl and R' is methyl. For example, the organic solvent may comprise cyclopentyl methyl ether.

In other embodiments, the organic solvent comprises a compound of the formula R—O—R' wherein R and R' are each $C_3$-$C_6$ alkyl. For example, the organic solvent may comprise dibutyl ether. In such embodiments, dibutyl ether forms peroxides at a much slower rate as compared to other ethereal solvents.

In further embodiments, steps other than the hydrolysis step described herein may be conducted in the presence of an organic solvent comprising an ester compound of the formula R—C(O)O—R' wherein R and R' are each independently selected from $C_1$-$C_6$ alkyl. For example, the organic solvent may comprise ethyl acetate, isopropyl acetate, butyl acetate, or isobutyl acetate.

Conversion of Thiophene to (thiophene-2-carbonyl)sulfamoyl Chloride

In various embodiments, the processes disclosed herein comprise a step wherein thiophene is reacted with chlorosulfonyl isocyanate (CSI) to produce (thiophene-2-carbonyl)sulfamoyl chloride (NCSAT).

In one embodiment, it has been observed that the chlorosulfonyl isocyanate reacts almost exclusively with the 2-position carbon of the thiophene ring. Other methods of thiophene substitution known in the art produce significant amounts of the 3-position isomer. In some embodiments, the reaction described herein can be used to produce (thiophene-2-carbonyl)sulfamoyl chloride in a molar ratio of at least about 99:1 in relation to the (thiophene-3-carbonyl)sulfamoyl chloride isomer.

Without being bound to a particular theory, in some embodiments, the reaction of thiophene and chlorosulfonyl isocyanate is believed to form N-(thiophen-2-ylsulfonyl)thiophene-2-carboxamide (NTSAT) as a byproduct. To minimize the formation of reaction byproducts, the reaction may be carried out with chlorosulfonyl isocyanate present in molar excess relative to thiophene. For example, the molar ratio of chlorosulfonyl isocyanate to thiophene, in terms of the amount of each reactant added to the reaction medium, may be greater than about 1.05:1, greater than about 1.1:1, greater than about 1.15:1, greater than about 1.2:1, or greater than about 1.25:1. In some embodiments, the molar ratio of chlorosulfonyl isocyanate to thiophene may be from about 1.05:1 to about 1.5:1, from about 1.05:1 to about 1.25:1, from about 1.05:1 to about 1.2:1, from about 1.05:1 to about 1.15:1, from about 1.1:1 to about 1.5:1, from about 1.1:1 to about 1.25:1, from about 1.1:1 to about 1.2:1, or from about 1.1:1 to about 1.15:1.

The reactants may be combined using a conventional order of addition, wherein the chlorosulfonyl isocyanate is added to thiophene. In certain embodiments, however, the reactants are combined using reverse addition, wherein the thiophene is added to chlorosulfonyl isocyanate. In some embodiments, the addition of thiophene to chlorosulfonyl isocyanate results in generation of fewer reaction byproducts and increases the yield of (thiophene-2-carbonyl)sulfamoyl chloride. In some embodiments, reverse addition of thiophene to chlorosulfonyl isocyanate, under conditions where chlorosulfonyl isocyanate is constantly present in molar excess during the reaction as described above, may promote conversion of thiophene to (thiophene-2-carbonyl)sulfamoyl chloride and minimize the production of NTSAT.

The reaction of thiophene with chlorosulfonyl isocyanate produces the reaction product (thiophene-2-carbonyl)sulfamoyl chloride, which may be present as a substantially homogenous solution in the organic solvent, as a solid suspension, or as a slurry in the organic solvent. In one embodiment, the reaction produces a substantially homogeneous reaction mixture in the organic solvent and thereafter the (thiophene-2-carbonyl)sulfamoyl chloride reaction product is retained as a solute in the organic solvent during and/or after the reaction. In some embodiments, the (thiophene-2-carbonyl)sulfamoyl chloride is not isolated from the homogenous reaction medium. In other embodiments, the (thiophene-2-carbonyl)sulfamoyl chloride is isolated from the homogenous reaction medium by distillation of the organic solvent or extraction. In another embodiment, the reaction initially produces a substantially homogeneous reaction mixture and thereafter the (thiophene-2-carbonyl)sulfamoyl chloride reaction product forms a solid precipitate. In some embodiments, when the reaction is substantially complete, the (thiophene-2-carbonyl)sulfamoyl chloride is retained in the reaction medium as a solid suspension or slurry in the organic solvent, and is not filtered or otherwise isolated from the reaction medium. In other embodiments, the solid suspension or slurry of the (thiophene-2-carbonyl)sulfamoyl chloride is isolated from the organic solvent by filtration, centrifugation, and/or decanting.

In some embodiments, the addition of chlorosulfonyl isocyanate to thiophene or the reverse addition of thiophene to chlorosulfonyl isocyanate as described herein may result in a solid precipitate that comprises greater than about 90 area % purity of (thiophene-2-carbonyl)sulfamoyl chloride as measured by a reverse phase high-performance liquid chromatography (RP-HPLC) method. In some embodiments, the solid precipitate may comprise greater than about 95 area %, greater than about 96 area %, greater than about 97 area %, greater than about 98 area %, or greater than about 99 area % purity of (thiophene-2-carbonyl)sulfamoyl chloride as measured by a RP-HPLC method.

In some embodiments, the reaction of thiophene with chlorosulfonyl isocyanate is carried out at a temperature of from about −20° C. to about 100° C., from about −20° C. to about 0° C., from about 0° C. to about 50° C., from about 35° C. to about 50° C., or from about 50° C. to about 100° C.

Conversion of (thiophene-2-carbonyl)sulfamoyl Chloride to 2-thiophenecarboxylic Acid In various embodiments, the processes disclosed herein further comprise a step wherein (thiophene-2-carbonyl)sulfamoyl chloride is hydrolyzed to produce 2-thiophenecarboxylic acid.

In some embodiments, the hydrolysis reaction is conducted in the presence of an acidic aqueous medium. For example, the acidic aqueous medium may comprise a strong acid, defined herein as an acid that completely or almost completely dissociates in water. Non-limiting examples of suitable acids include mineral acids such as hydrochloric acid and sulfuric acid. In some embodiments, the concentration of hydrochloric acid in the aqueous solution is from about 1 M to about 12 M, or from about 3 percent by weight (wt %) to about 37 wt %. In other embodiments, the concentration of sulfuric acid in the aqueous solution is from about 1 M to about 18 M, or from 5 wt % to about 95 wt %.

In some embodiments, (thiophene-2-carbonyl)sulfamoyl chloride, present in the form of homogenous solution, a suspension or slurry in the organic solvent as described herein, is added to the acidic aqueous medium. In other embodiments, (thiophene-2-carbonyl)sulfamoyl chloride, present in the form of isolated solids as described herein, is added to an acidic aqueous medium and additional organic solvent (e.g., dibutyl ether) is added to the resulting reaction medium. In some embodiments, the resulting reaction medium is biphasic at or near room temperature, but can become substantially homogeneous at or above a temperature of about 100° C.

In some embodiments, the volumetric ratio of the organic solvent to the aqueous acidic medium is from about 3:4 to about 1:1. In other embodiments, the volumetric ratio of the organic solvent to the aqueous acidic medium is from about 1:2 to about 1:1, from about 2:3 to about 1:1, or from about 1:4 to about 1:1.

Because the reaction is exothermic, the acidic aqueous medium may be chilled to below ambient temperature prior to combination with the (thiophene-2-carbonyl)sulfamoyl chloride suspension, slurry, or isolated solid in order to control the exotherm. For example, the acidic aqueous medium may be chilled to a temperature of from about 0° C. to about 10° C. In some embodiments, during the initial exothermic reaction, the temperature of the reaction medium is maintained at a temperature below about 50° C., for example from about 30° C. to about 50° C. Rapidly stirring the acidic aqueous medium before and/or during the reaction may also be helpful to control the exotherm and maintain a consistent temperature throughout the reaction medium. In some embodiments, the temperature of the reaction medium during the hydrolysis reaction, wherein the organic solvent (e.g., dibutyl ether) is raised to a temperature of at least about 50° C. For example, in some embodiments, the temperature is maintained at from about 50° C. to about 130° C., from about 70° C. to about 115° C., from about 90° C. to about 110° C., or at least about 80° C.

In some embodiments, the hydrolysis reaction is conducted in the presence of a basic aqueous medium. For example, the basic aqueous medium may comprise a strong base, defined herein as a base that completely or almost completely dissociates in water. Non-limiting examples of suitable bases include alkali or alkaline earth hydroxides such as sodium hydroxide, potassium hydroxide and mixtures thereof. In some embodiments, the concentration of sodium hydroxide in the aqueous solution is from about 1 M to about 20 M, or from about 2.5 wt % to about 50 wt %. In other embodiments, the concentration of potassium hydroxide in the aqueous solution is from about 1 M to about 12 M, or from 4 wt % to about 45 wt %. A neutralization step is conducted to convert a salt form of 2-thiophenecarboxylic acid from the base hydrolysis with an acid to the 2-thiophenecarboxylic acid.

In some embodiments, the hydrolysis reaction is conducted initially in the presence of an aqueous medium to form 2-thiophenecarboxamide (TCAm) as an intermediate, wherein the aqueous medium comprises water. The intermediate 2-thiophenecarboxamide (TCAm) is further hydrolyzed in the presence of an acidic aqueous medium or a basic aqueous medium. The acidic aqueous medium may comprise a strong acid and the basic aqueous medium may comprise a strong base, as defined above. In some embodiments, the hydrolysis reaction is initiated by contacting water to form 2-thiophenecarboxamide (TCAm) and further hydrolyzed in the presence of a strong acid selected from the group consist of hydrochloric acid and sulfuric acid. In some embodiments, the concentration of hydrochloric acid in the aqueous solution is from about 1 M to about 12 M, or from about 3 wt % to about 37 wt %. In other embodiments, the concentration of sulfuric acid in the aqueous solution is from about 1 M to about 18 M, or from 5 wt % to about 95 wt %. In some other embodiments, the hydrolysis reaction is initiated by contacting water to form 2-thiophenecarboxamide (TCAm) and further hydrolyzed in the presence of a strong base selected from the group consist of sodium hydroxide, potassium hydroxide and mixtures thereof. In some embodiments, the concentration of sodium hydroxide in the aqueous solution is from about 1 M to about 20 M, or from about 2.5 wt % to about 50 wt %. In other embodiments, the concentration of potassium hydroxide in the aqueous solution is from about 1 M to about 12 M, or from 4 wt % to about 45 wt %.

Without being bound to a particular theory, in some embodiments, the reaction of the (thiophene-2-carbonyl)sulfamoyl chloride and the acidic medium is believed to form 2-thiophenecarboxamide (TCAm) as an intermediate. It is important to achieve complete or substantially complete hydrolysis of 2-thiophenecarboxamide to avoid the formation of undesirable byproducts such as 2-thiophenecarbonitrile in subsequent process steps. In some embodiments, wherein the acid in the hydrolysis reaction comprises hydrochloric acid or sulfuric acid, the substantially complete hydrolysis of 2-thiophenecarboxamide may be advantageously attained.

In some embodiments, once the reaction is substantially complete, the reaction medium separates into an organic phase comprising the 2-thiophenecarboxylic acid reaction product and an aqueous phase. The organic phase can then be separated using means known in the art, for example by decantation. In some embodiments, additional organic solvent is used to extract the 2-thiophenecarboxylic acid partially remaining in the aqueous phase to achieve more recovery of the product.

In some embodiments, the 2-thiophenecarboxylic acid reaction product remains soluble in the organic phase so long as the temperature of the organic phase is maintained sufficiently high (e.g., at temperatures at or above about 60° C. in some of the solvents as described herein). Accordingly, once the reaction is substantially complete, the organic phase is typically maintained at a temperature sufficiently high to prevent undesired precipitation of the 2-thiophenecarboxylic acid prior to separation of the organic phase.

Conversion of 2-thiophenecarboxylic Acid to 2-thiophenecarbonyl Chloride

In various embodiments, the processes disclosed herein further comprise a chlorination step wherein 2-thiophenecarboxylic acid is reacted with a chlorinating reagent to produce the 2-thiophenecarbonyl chloride product. Non-limiting examples of chlorinating agents include thionyl chloride, oxalyl chloride, $POCl_3$, $PCl_5$, phosgene, and other chlorinating agents known in the art. For example, in some embodiments, the chlorinating agent is thionyl chloride.

The 2-thiophenecarboxylic acid may be present in the form of a solute in the organic solvent as described herein. In some embodiments, the thionyl chloride is added to a liquid reaction medium comprising the 2-thiophenecarboxylic acid dissolved in the organic solvent. In some embodiments, the reaction mixture is initially heterogeneous or multi-phasic, but becomes substantially homogeneous or monophasic after a sufficient portion of the chlorinating reagent has been added.

In some embodiments, the reaction may be carried out in the presence of a catalyst that promotes the formation of the 2-thiophenecarbonyl chloride product. Non-limiting examples of catalysts include amides, imides, amines, quaternary ammonium salts and ureas. For example, in some embodiments, the reaction medium may comprise an N,N-disubstituted amide such as N,N-dimethyl formamide or N-methylpyrrolidone; a N-monosubstituted amide such as N-methyl formamide or N-methylacetamide; a tertiary amine such as pyridine or triethylamine; a secondary amine such as pyrrolidine or diethylamine; and/or a substituted urea such as tetramethyl urea. For example, in some embodiments, the reaction medium comprises a catalytic amount of N,N-dimethylformamide, wherein the molar percentage of N,N-dimethylformamide to 2-thiophenecarboxylic acid is from about 1 mol % to about 5 mol %.

To maximize the conversion of 2-thiophenecarboxylic acid to 2-thiophenecarbonyl chloride, the reaction may be carried out with the chlorinating reagent present in molar excess relative to 2-thiophenecarboxylic acid. In some embodiments, the molar ratio of chlorinating reagent to 2-thiophenecarboxylic acid, in terms of the amount of each reactant added to the reaction medium, is less than about 2:1. For example, in some embodiments, the molar ratio of of chlorinating reagent to 2-thiophenecarboxylic acid, in terms of the amount of each reactant added to the reaction medium, is from about 1:1 to about 2:1, from about 1.5:1 to about 2:1, from about 1.1:1 to about 1.5:1, or from about 1.1:1 to about 1.25:1.

Without being bound to a particular theory, in some embodiments wherein the chlorinating reagent comprises thionyl chloride, the thionyl chloride may react with 2-thiophenecarboxamide present along with 2-thiophenecarboxylic acid in the reaction medium from the hydrolysis step to form 2-thiophenecarbonitrile as a byproduct. As noted above, the formation of 2-thiophenecarbonitrile can be minimized by ensuring that substantially all 2-thiophenecarboxamide produced in the hydrolysis step has been hydrolyzed to form 2-thiophenecarboxylic acid before initiating the reaction with thionyl chloride.

In some embodiments, the reaction of 2-thiophenecarboxylic acid with the chlorinating agent is carried out at a temperature below the boiling point of the organic solvent present in the reaction medium. In some embodiments, the reaction of 2-thiophenecarboxylic acid with the chlorinating reagent is carried out at a temperature of from about 50° C. to about 80° C., or from about 60° C. to about 70° C.

Recovery of 2-thiophenecarbonyl Chloride

In various embodiments, the processes disclosed herein further comprise a step wherein the 2-thiophenecarbonyl chloride product is recovered by distillation of the liquid medium.

In one embodiment, if the 2-thiophenecarbonyl chloride is produced by reacting 2-thiophenecarboxylic acid with thionyl chloride as described above, it is preferable to ensure that the HCl and $SO_2$ gas products of the chlorination reaction have fully evolved from the liquid medium before starting the distillation process. In another embodiment, the reaction medium is maintained at a temperature from about 40° C. to about 60° C. and placed under vacuum for a time sufficient to ensure that the gas products of the chlorination reaction are substantially removed from the liquid medium.

Separation of the organic solvent and the 2-thiophenecarbonyl chloride product may be carried out using methods known in the art, including but not limited to simple distillation or fractional distillation. An initial distillation stage may be operated to remove and recover the solvent. Suitable distillation temperature and pressure conditions for the removal and recovery of the organic solvent will be apparent to those skilled in the art. In some embodiments, wherein the solvent comprises dibutyl ether, the initial distillation is conducted at a bath temperature of about 100° C. to about 110° C. under vacuum (e.g., about 30 mmHg; 4 kPa).

Recovery of the 2-thiophenecarbonyl chloride product may then be achieved by purification methods known in the art. For example, in some embodiments, the remaining liquid medium is distilled using vacuum or fractional distillation. In some embodiments, the 2-thiophenecarbonyl chloride product is recovered by distilling the remaining liquid medium under high vacuum. Suitable distillation temperature and pressure conditions for the recovery of the 2-thiophenecarbonyl chloride product will be apparent to those skilled in the art.

Production of 3,5-disubstituted 1,2,4-oxadiazoles

In various embodiments, the process may further comprise steps for producing a 3,5-disubstituted 1,2,4-oxadiazole or a salt thereof. Methods for the preparation of 3,5-disubstituted-1,2,4-oxadiazoles that utilize acyl chlorides as a starting material are disclosed in U.S. Pub. No. 2014/0039197 A1, the entire contents of which are herein incorporated by reference.

The following examples are to be considered as merely illustrative, and are not intended to limit the scope of this disclosure.

Example 1: Analytical Methods

A. Reverse-Phase High-Performance Liquid Chromatography (RP-HPLC) Method

RP-HPLC analysis used to monitor reactions was conducted on an Agilent 1260 Infinity Analytical-Scale LC/MS Purification System equipped with a diode array UV detector and monitored at 230 nm and 280 nm.

B. Nuclear Magnetic Resonance Method

Nuclear magnetic resonance analysis was run on a Bruker 600 MHz instrument. Deuterated solvents from Cambridge Isotope Laboratories, Ltd., including methanol-$d_4$, chloroform-d, and dimethylsulfoxide-$d_6$, were used as required.

C. Gas Chromatography Flame Ionization Detection (GC-FID) Method

Gas Chromatography Flame Ionization Detection (GC-FID) analysis was used to determine the purity and impurity profiles of thiophene-2-carbonyl chloride. Thiophene-2-carbonyl chloride samples were diluted in hexane and analyzed on an Agilent 7890B GC-FID system with Agilent 7693 autosampler.

Example 2: Preparation of (Thiophene-2-carbonyl)sulfamoyl Chloride From Thiophene

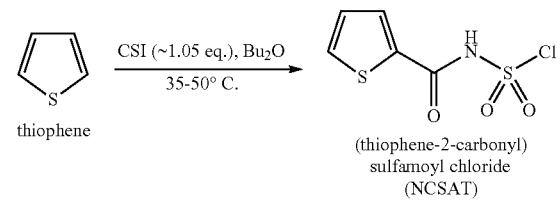 [SMILES: c1ccsc1 ; O=C(NS(=O)(=O)Cl)c1cccs1]

thiophene (thiophene-2-carbonyl) sulfamoyl chloride (NCSAT)

A. Addition by Adding Chlorosulfonyl Isocyanate (CSI) to Thiophene

A portion of CSI (7.6 mL) was added at once into a solution of thiophene (21.0 g, 0.25 mol) in dibutyl ether ($Bu_2O$) (30 mL), and the reaction temperature increased from room temperature to 30° C. Additional CSI (15.2 mL) was added portion-wise (1 mL every 5 minutes) during which the internal temperature increased from 35° C. to 50° C. and was kept below 50° C. by cooling with a water-bath. After completion of addition, the resulting mixture was stirred at 50° C. for additional one hour. The reaction mixture was homogenous initially and became heterogeneous with solid precipitations after an approximate ⅔ portion of total CSI was added. The resulting precipitate was filtered. The filtered solids were washed with toluene and dried under vacuum to afford the title compound as a white solid (41 g, 75%). RP-HPLC and ¹H NMR (600 MHz, chloroform-d) confirmed that the obtained material was (thiophene-2-carbonyl)sulfamoyl chloride with a purity of 92%. ¹H-NMR (600 MHz, chloroform-d) δ 9.4-9.3 (br s, 1H), 7.8 (m, 1H), 7.75 (m, 1H), 7.22 (m, 1H).

B. Reverse Addition by Adding Thiophene to Chlorosulfonyl Isocyanate (CSI)

A solution of thiophene (5.0 g, 0.06 mol) in dibutyl ether (5 mL) was added dropwise via a dropping funnel into a solution of CSI (8.7 g, 1.03 eq.) in dibutyl ether (10 mL) over 45 minutes, during which the reaction temperature increased from room temperature to 27° C. After completion of addition, the resulting mixture was warmed up to 48° C. and stirred for 1.5 hours. The resulting mixture was taken directly for acid hydrolysis using aqueous sulfuric acid (20%).

The mixture was added into aqueous sulfuric acid (20%, 20 mL) while keeping the reaction flask in an ice-bath due to an exothermic reaction. After completion of the addition, the reaction mixture was heated at 110° C. for 3 hours. After being cooled to 60° C., the layers were separated. The aqueous layer was extracted with dibutyl ether (1×10 mL), and the combined organic layers were concentrated in vacuo to afford 2-thiophenecarboxylic acid as a white solid (4.0 g, 53%).

C. Impurity Comparison of Two Addition Methods

The impurity profiles of two addition methods used to form (thiophene-2-carbonyl)sulfamoyl chloride (NCSAT) from thiophene were compared. The side product as N-(thiophen-2-ylsulfonyl)thiophene-2-carboxamide (NTSAT) was observed to be less than about 4 area % when the reverse addition method was used. Addition of CSI to thiophene is very selective (>99:1) at the 2-position of thiophene for both addition methods. The results of these two addition methods are provided in Table 2.

TABLE 2

Purity Profile of NCSAT by HPLC via Two Addition Methods

| Addition Method | Purity of NCSAT (Area % by HPLC)) | Impurity NTSAT (Area % by HPLC) | Selectivity at 2-position (%) |
|---|---|---|---|
| Addition (CSI to thiophene) | 92 | 8 | >99 |
| Reverse Addition (Thiophene to CSI) | 96 | 4 | >99 |

Example 3: Hydrolysis of (Thiophene-2-carbonyl)sulfamoyl Chloride to form 2-thiophenecarboxylic Acid

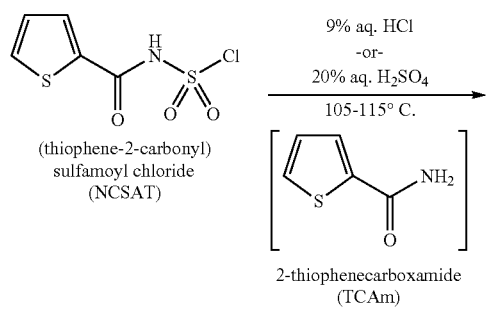

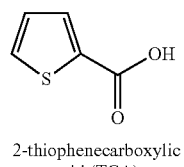
2-thiophenecarboxylic acid (TCA)

A. Hydrolysis using Aqueous Sulfuric Acid (20%)

(Thiophene-2-carbonyl)sulfamoyl chloride (10.0 g, 0.044 mol), prepared by Example 2-A, was suspended in a mixture of aqueous sulfuric acid (20%, 40 mL) and dibutyl ether (10 mL). The reaction mixture was kept below 40° C. with a water-bath due to an initial exothermic reaction. After the initial exothermic reaction, the reaction mixture was heated at 110° C. for 2 hours. The reaction mixture became homogenous once the internal temperature reached 90° C. After being cooled to 75° C., the layers were separated. The aqueous layer was extracted with dibutyl ether (2×10 mL), and the combined organic layers were concentrated in vacuo to afford 2-thiophenecarboxylic acid as a white solid (5.2 g, 91%). RP-HPLC and ¹H NMR (600 MHz, DMSO-d₆) confirmed that the obtained material was 2-thiophenecarboxylic acid acid with a purity of 97 area %. ¹H-NMR (600 MHz, DMSO-d₆) δ 12-11 (br s, 1H), 7.87 (m, 1H), 7.74 (m, 1H), 7.18 (m, 1H); ESI-MS m/z 128.9 (M+H).

B. Hydrolysis using Aqueous Hydrochloric Acid (3 M, 9%)

(Thiophene-2-carbonyl)sulfamoyl chloride (10.0 g, 0.044 mol), prepared by Example 2-A, was suspended in aqueous hydrochloride acid (3 M, 40 mL). Dibutyl ether (10 mL) was added to the mixture and the resulting reaction mixture was heated to reflux. The reaction mixture became homogenous once the internal temperature reached 90° C. After heating for 7 hours, the RP-HPLC showed that 2-thiophenecarboxamide (TCAm), as the hydrolysis intermediate, was detected to be <0.1 area %. After being cooled to 75° C., the layers were separated. The aqueous layer was extracted with dibutyl ether (2×10 mL), and the combined organic layers were concentrated in vacuo to afford 2-thiophenecarboxylic acid as a white solid (5.5 g, 97%). The RP-HPLC indicated that the isolated 2-thiophenecarboxylic acid had a purity of 99 area %.

C. Impurity Comparison of Two Hydrolysis Methods

The impurity profiles of two hydrolysis methods used to form 2-thiophenecarboxylic acid (TCA) from (thiophene-2-carbonyl)sulfamoyl chloride (NCSAT) were compared. 2-thiophenecarboxamide (TCAm), an incomplete hydrolysis side product, was converted into 2-thiophenecarbonitrile during the next acetylation step with thionyl chloride. 2-thiophenecarbonitrile was an undesirable impurity in the final 2-thiophenecarbonyl chloride product, therefore it was important to minimize 2-thiophenecarboxamide (TCAm) during the hydrolysis. Hydrolysis using aqueous hydrochloride acid (3 M) was observed to produce 2-thiophenecarboxamide (TCAm) that was less than about 0.1 area %. The previous impurity N-(thiophen-2-ylsulfonyl)thiophene-2-carboxamide (NTSAT) remained in the product TCA since it is not hydrolyzed. The results of these two hydrolysis methods are provided in Table 3.

TABLE 3

Purity Profile of TCA by HPLC via Two Hydrolysis Methods

| Hydrolysis Method | Purity of TCA (Area % by HPLC) | Impurity TCAm (Area % by HPLC) | NTSAT |
|---|---|---|---|
| aqueous sulfuric acid (20%) | 95 | 2.8 | Remain |
| aqueous hydrochloride acid (3M) | 97 | <0.1 | Remain |

Example 4: Conversion of 2-Thiophenecarboxylic Acid to 2-Thiophenecarbonyl Chloride

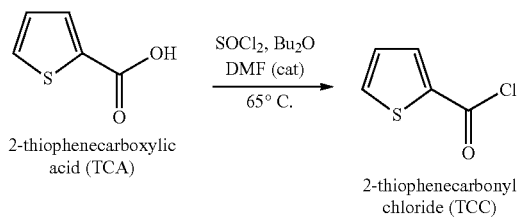 [SMILES: O=C(O)c1cccs1 ; O=C(Cl)c1cccs1]

2-thiophenecarboxylic acid (7.1 g, 0.055 mol), prepared by Example 3-A, was suspended in dibutyl ether (25 mL). A catalytic amount of dimethylformamide (DMF) (0.2 mL, 0.05 eq.) was added followed by a slow addition of thionyl chloride (SOCl₂) (4.4 mL, 1.1 eq.). During the addition, gases such as sulfur dioxide (SO₂) and hydrogen chloride (HCl) were released. The resulting mixture was heated at 65° C. for 1 hour after completion of the addition, followed by cooling to ambient temperature. Vacuum distillation (short path, 25 mmHg) gave dibutyl ether (~22 mL), which was distilled from the mixture at a vapor temperature of 80° C. while the bath temperature was at 100° C. The remaining mixture was cooled to room temperature and switched to a higher vacuum. Distillation (short path, 2 mmHg) at a vapor temperature of 40° C. (bath temperature was at 60° C.) afforded 2-thiophenecarbonyl chloride as a clear oil (6.0 g, 74%). GC-FID and ¹H NMR (600 MHz, chloroform-d) confirmed that the obtained material was 2-thiophenecarbonyl chloride with a purity of 97 area %. ¹H NMR spectrum indicated the final product contained Bu₂O in about 3% and aromatic impurities of <1%. ¹H-NMR (600 MHz, chloroform-d) δ 8.01 (dd, 1H, J=4.0, 2.6 Hz), 7.85 (dd, 1H, J=5.0, 1.3 Hz), 7.23 (dd, 1H, J=5.0, 4.0 Hz).

Example 5: Alternative Preparation of 2-Thiophenecarbonyl Chloride From Thiophene (Sulfuric Acid Hydrolysis)

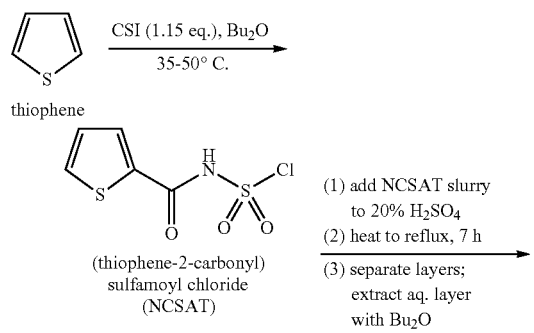

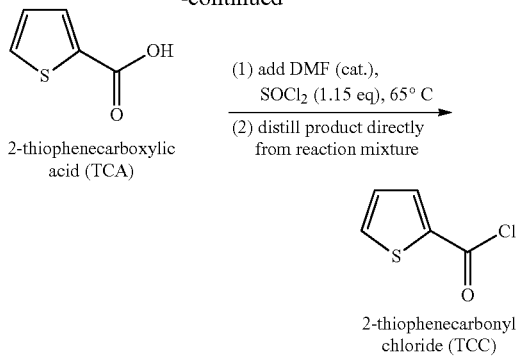

A solution of CSI (35.7 mL, 1.15 eq.) in dibutyl ether (50 mL) was first heated to 40° C. A solution of thiophene (30 g, 0.36 mol) in dibutyl ether (10 mL) was added dropwise via a dropping funnel into the solution of CSI over 60 minutes. After addition of about 60% of thiophene, white precipitate was formed in the reaction mixture. After completion of addition, the resulting mixture was heated at 50° C. for 2.5 hours. The resulting mixture (the first mixture) was taken directly for acid hydrolysis using aqueous sulfuric acid (20%).

Aqueous sulfuric acid (20%, 120 mL) in a round-bottom flask was cooled with an ice-bath while stirring. The aforementioned first mixture was slowly added into the chilled aqueous sulfuric acid, during which the internal temperature was kept below 50° C. After completion of the addition, dibutyl ether (20 mL) was used to rinse the remaining of the first mixture and then added to the sulfuric mixture. The reaction mixture (the second mixture) was heated to reflux (~110° C.). After heating for 7 hours, the RP-HPLC showed that 2-thiophenecarboxamide (TCAm), as the hydrolysis intermediate, was detected to be <3 area %. After being cooled to 70° C., the layers were separated. The aqueous layer was extracted with hot (70° C.) dibutyl ether (2×20 mL), and the combined organic layers were washed with water (1×15 mL) while the temperature of the organic layer was kept above 60° C. The resulting mixture of the organic layer (the third mixture) was taken directly for acyl chloride formation with thionyl chloride.

DMF (1.2 mL, 15 mmol) was added in a single portion to the aforementioned third mixture. Thionyl chloride (SOCl₂) (30 mL, 0.41 mol) was added dropwise via a dropping funnel to the reaction mixture that was preheated to 65° C. During the addition, the released sulfur dioxide (SO₂) and hydrogen chloride (HCl) were captured with an aqueous base trap. The resulting mixture was heated at 65° C. for additional 1 hour after completion of the addition. The reaction system was attached with a short path distillation head and a vigreux column, and then placed under a vacuum (300 to 30 mmHg). After removing gases in the reaction mixture by applying an initial vacuum (300 mmHg), the mixture was then heated to 100° C. under a vacuum (30 mmHg). After dibutyl ether (~60 mL) was distilled from the mixture, the remaining mixture was switched to a higher vacuum (5 mmHg). Distillation at a vapor temperature of 50-60° C. (bath temperature was at ~110° C.) afforded 2-thiophenecarbonyl chloride as a clear oil (34.0 g, 65%). GC-FID and ¹H NMR (600 MHz, chloroform-d) confirmed that the obtained material was 2-thiophenecarbonyl chloride with a purity of 98 area %. ¹H NMR spectrum indicated the final product was free of dibutyl ether.

Example 6: Alternative Preparation of 2-Thiophenecarbonyl Chloride From Thiophene (Hydrochloride Acid Hydrolysis)

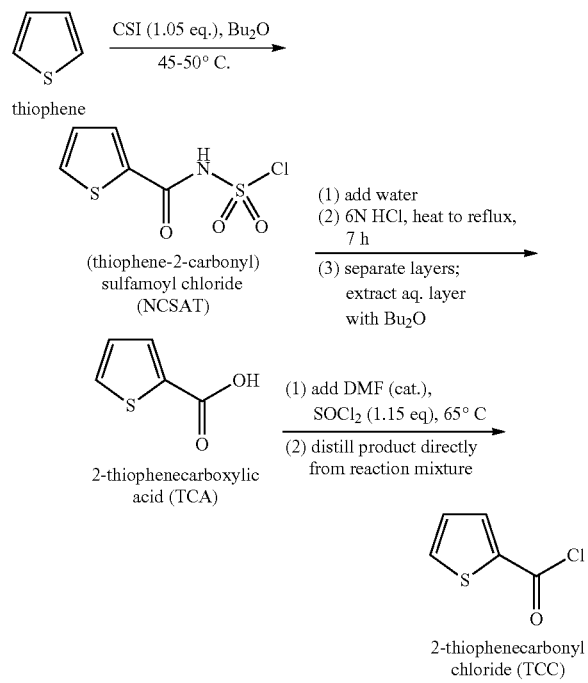

A solution of thiophene (50.0 g, 0.59 moles) in dibutyl ether (100 mL) was heated to 45-50° C. CSI (88.7 g, 0.63 moles, 1.05 eq.) was added dropwise via a dropping funnel into the solution of tiophene over 77 minutes. White precipitate was formed in the reaction mixture near the end of the addition and additional dibutyl ether (100 mL) was added to maintain the stirring of the slurry. The temperature was raised to 65° C. to complete the reaction. At 7.8 hours, RP-HPLC analysis showed that only 1.3% of unreacted thiophene remained. The resulting mixture (the first mixture) was taken directly for acid hydrolysis using aqueous hydrochloride acid.

Water (50 g) was added slowly to moderate the strongly exothermic hydrolysis reaction, forming 2-thiophenecarboxamide. Aqueous HCl solution (6N, 345.0 g, 1.88 moles HCl) was added over 15 minutes, and the reaction mixture was heated to 100° C. for 7 hours to convert the 2-thiophenecarboxamide to 2-thiophenecarboxylic acid. The layers were separated while hot and the aqueous phase was extracted with dibutyl ether (3×50 mL). The empty reaction vessel was rinsed with dibutyl ether (25 mL) to recover the remaining 2-thiophenecarboxylic acid solids. The dibutyl ether layers were combined and used directly for acyl chloride formation with thionyl chloride.

The dibutyl ether mixture of 2-thiophenecarboxylic acid from above (338.8 g), along with DMF (1.92 g, 0.026 moles), was heated to 65° C. Thionyl chloride (81.56 g, 0.68 moles) was added via a dropping funnel over one hour, during which there was a steady evolution of gas. The GC-FID showed that there was no remaining 2-thiophenecarboxylic acid after 1.5 hours. The dissolved gases and most of the dibutyl ether were removed by distillation at 35-40° C. under a vacuum (20 mmHg). The remaining dibutyl ether was removed using a vacuum pump. The product, 2-thiophene carbonyl chloride, was distilled at 47° C. under a vacuum (2 mmHg) as a colorless oil (56.20 g, 63.5%). GC-FID confirmed that the obtained material was 2-thiophenecarbonyl chloride with a purity of 98.4 area %.

Embodiments

For further illustration, additional non-limiting embodiments of the present disclosure are set forth below.

For example, embodiment 1 is a process for preparing 2-thiophenecarbonyl chloride, the process comprising:
reacting thiophene with chlorosulfonyl isocyanate in a reaction medium comprising an organic solvent, thereby producing (thiophene-2-carbonyl)sulfamoyl chloride,
wherein the reaction is initiated by mixing the thiophene and the chlorosulfonyl isocyanate,
and wherein the chlorosulfonyl isocyanate is present in molar excess relative to thiophene.

Embodiment 2 is the process of embodiment 1 wherein the organic solvent comprises a compound selected from the group consisting of $C_1$-$C_{10}$ alkane solvents, $C_1$-$C_{10}$ halogenated alkane solvents, $C_1$-$C_{10}$ alkylbenzenes, halogenated aromatic solvents, and dialkyl ether solvents of the general formula R—O—R', wherein R and R' are each independently selected from $C_1$-$C_6$ alkyl.

Embodiment 3 is the process of embodiment 1 wherein the organic solvent comprises a compound of the formula R—O—R' wherein R is selected from $C_4$-$C_6$ cycloalkyl and R' is methyl.

Embodiment 4 is the process of embodiment 1 wherein the organic solvent comprises cyclopentyl methyl ether.

Embodiment 5 is the process of embodiment 1 wherein the organic solvent comprises a compound of the formula R—O—R' wherein R and R' are each $C_3$-$C_6$ alkyl.

Embodiment 6 is the process of embodiment 1 wherein the organic solvent comprises dibutyl ether.

Embodiment 7 is a process for preparing 2-thiophenecarbonyl chloride, the process comprising:
reacting thiophene with chlorosulfonyl isocyanate in a reaction medium comprising an organic solvent, thereby producing (thiophene-2-carbonyl)sulfamoyl chloride,
wherein the organic solvent comprises dibutyl ether.

Embodiment 8 is the process of any one of embodiments 1 to 7 wherein the reaction is initiated by adding the thiophene to the chlorosulfonyl isocyanate, and wherein the chlorosulfonyl isocyanate is present in molar excess relative to the thiophene.

Embodiment 9 is the process of any one of embodiments 1 to 7 wherein the reaction is initiated by adding the chlorosulfonyl isocyanate to the thiophene, and wherein the chlorosulfonyl isocyanate is present in molar excess relative to the thiophene.

Embodiment 10 is the process of any one of embodiments 1 to 9 wherein the molar ratio of chlorosulfonyl isocyanate to thiophene is from about 1.05:1 to about 1.5:1, from about 1.05:1 to about 1.25:1, from about 1.05:1 to about 1.2:1, from about 1.05:1 to about 1.15:1, from about 1.1:1 to about 1.5:1, from about 1.1:1 to about 1.25:1, from about 1.1:1 to about 1.2:1, or from about 1.1:1 to about 1.15:1.

Embodiment 11 is the process of any one of embodiments 1 to 10 wherein the (thiophene-2-carbonyl)sulfamoyl chloride is maintained as a substantially homogenous solution in a liquid organic phase comprising the organic solvent.

Embodiment 12 is the process of any one of embodiments 1 to 11 wherein the (thiophene-2-carbonyl)sulfamoyl chloride is maintained as a solid suspension in a liquid organic phase comprising the organic solvent.

Embodiment 13 is the process of any one of embodiments 1 to 12 wherein the (thiophene-2-carbonyl)sulfamoyl chloride is isolated as a solid by filtration, centrifugation, and/or decantation.

Embodiment 14 is the process of any one of embodiments 1 to 13 wherein the reaction is carried out at a temperature of from about −20° C. to about 100° C., from about 0° C. to about 50° C., or from about 35° C. to about 50° C.

Embodiment 15 is the process of any one of embodiments 1 to 14 further comprising a hydrolysis reaction step in which (thiophene-2-carbonyl)sulfamoyl chloride is hydrolyzed to produce 2-thiophenecarboxylic acid.

Embodiment 16 is the process of embodiment 15 wherein the hydrolysis reaction is initiated by adding (thiophene-2-carbonyl)sulfamoyl chloride to an aqueous medium comprising a strong acid, wherein the (thiophene-2-carbonyl)sulfamoyl chloride is present in the form of a substantially homogenous solution, in the form of an isolated solid, or in the form of a solid suspension in a liquid organic phase comprising the organic solvent.

Embodiment 17 is the process of embodiment 16 wherein the (thiophene-2-carbonyl)sulfamoyl chloride is present in the form of a substantially homogenous solution in a liquid organic phase comprising the organic solvent.

Embodiment 18 is the process of embodiment 16 wherein the (thiophene-2-carbonyl)sulfamoyl chloride is present in the form of an isolated solid.

Embodiment 19 is the process of embodiment 16 wherein the (thiophene-2-carbonyl)sulfamoyl chloride is present in the form of a solid suspension in a liquid organic phase comprising the organic solvent.

Embodiment 20 is the process of embodiment 16 wherein the strong acid comprises a compound selected form the group consisting of hydrochloric acid and sulfuric acid.

Embodiment 21 is the process of embodiment 20 wherein the strong acid comprises hydrochloric acid.

Embodiment 22 is the process of embodiment 21 wherein the hydrochloric acid has a concentration of from about 1 M to about 12 M, or from about 3 wt % to about 37 wt %.

Embodiment 23 is the process of embodiment 20 wherein the strong acid comprises sulfuric acid.

Embodiment 24 is the process of embodiment 23 wherein the sulfuric acid has a concentration of from about 1 M to about 18 M, or from 5 wt % to about 95 wt %.

Embodiment 25 is the process of any one of embodiments 16 to 24 wherein an organic solvent is added to the medium comprising the (thiophene-2-carbonyl)sulfamoyl chloride and the strong acid to form an acidic reaction medium.

Embodiment 26 is the process of embodiment 25 wherein the organic solvent comprises dibutyl ether.

Embodiment 27 is the process of any one of embodiments 16 to 26 wherein the volumetric ratio of the organic solvent and the acid aqueous medium is from about 1:4 to about 1:1, from about 1:2 to about 1:1, from about 2:3 to about 1:1, or from about 3:4 to about 1:1.

Embodiment 28 is the process of any one of embodiments 25 to 27 wherein the acidic reaction medium is heated at a temperature of at least about 80° C.

Embodiment 29 is the process of embodiment 28 wherein the temperature of the acidic reaction medium is maintained from about 50° C. to about 130° C., or from about 70° C. to about 115° C. during the hydrolysis step.

Embodiment 30 is the process of embodiment 15 wherein the hydrolysis reaction is initiated by adding (thiophene-2-carbonyl)sulfamoyl chloride to a basic medium comprising a strong base, wherein the (thiophene-2-carbonyl)sulfamoyl chloride is present in the form of a substantially homogenous solution, in the form of an isolated solid, or in the form of a solid suspension in a liquid organic phase comprising the organic solvent.

Embodiment 31 is the process of embodiment 30 wherein the strong base comprises a compound selected form the group consisting of sodium hydroxide and potassium hydroxide.

Embodiment 32 is the process of embodiment 31 wherein the strong base comprises sodium hydroxide.

Embodiment 33 is the process of embodiment 32 wherein the sodium hydroxide has a concentration of from about 1 M to about 20 M, or from about 2.5 wt % to about 50 wt %.

Embodiment 34 is the process of embodiment 31 wherein the strong acid comprises potassium hydroxide.

Embodiment 35 is the process of embodiment 34 wherein the potassium hydroxide has a concentration of from about 1 M to about 12 M, or from 4 wt % to about 45 wt %.

Embodiment 36 is the process of embodiment 30 further comprising a neutralization step in which a salt form of 2-thiophenecarboxylic acid from the base hydrolysis is neutralized with an acid to the 2-thiophenecarboxylic acid.

Embodiment 37 is the process of any one of embodiments 16 to 36 wherein the reaction medium is allowed to separate into an aqueous phase and an organic phase comprising 2-thiophenecarboxylic acid, and wherein the organic phase comprising 2-thiophenecarboxylic acid is separated from the aqueous phase.

Embodiment 38 is the process of embodiment 37 wherein the organic phase comprising 2-thiophenecarboxylic acid is separated from the aqueous phase using decantation.

Embodiment 39 is the process of embodiment 38 wherein the organic phase is maintained at a temperature of at least about 60° C. or at least about 70° C. during the decantation step.

Embodiment 40 is the process of any one of embodiments 1 to 39 further comprising a chlorination step in which 2-thiophenecarboxylic acid dissolved in the organic solvent is reacted with a chlorinating agent to produce 2-thiophenecarbonyl chloride in a liquid medium.

Embodiment 41 is the process of embodiment 40 wherein the chlorinating agent comprises thionyl chloride.

Embodiment 42 is the process of embodiment 41 wherein the chlorination reaction is initiated by adding a first liquid medium comprising thionyl chloride to a second liquid medium comprising 2-thiophenecarboxylic acid, wherein the second liquid medium comprises 2-thiophenecarboxylic acid dissolved in the organic solvent.

Embodiment 43 is the process of embodiment 42 wherein the chlorination reaction is carried out in the presence of a catalyst that promotes formation of 2-thiophenecarbonyl chloride.

Embodiment 44 is the process of embodiment 43 wherein the catalyst comprises dimethylformamide.

Embodiment 45 is the process of embodiment 44 wherein the molar percentage of N,N-dimethylformamide to 2-thiophenecarboxylic acid is from about 1 mol % to about 5 mol %.

Embodiment 46 is the process of any one of embodiments 42 to 45 wherein the chlorination reaction is carried out with the thionyl chloride present in molar excess relative to 2-thiophenecarboxylic acid.

Embodiment 47 is the process of embodiment 46 wherein the molar ratio of thionyl chloride to 2-thiophenecarboxylic acid is from about 1:1 to about 2:1, from about 1.5:1 to about 2:1, from about 1.1:1 to about 1.5:1, or from about 1.1:1 to about 1.25:1.

Embodiment 48 is the process of any one of embodiments 42 to 47 wherein the chlorination reaction is carried out at a temperature of from about 50° C. to about 80° C., or from about 60° C. to about 70° C.

Embodiment 49 is the process of any one of embodiments 1 to 48 further comprising a distillation step in which 2-thiophenecarbonyl chloride is recovered by distillation of the liquid medium.

Embodiment 50 is the process of embodiment 49 wherein the distillation comprises a solvent removal step.

Embodiment 51 is a process for preparing 2-thiophenecarbonyl chloride, the process comprising:

mixing a first liquid medium comprising thiophene dissolved in dibutyl ether and a second liquid medium comprising chlorosulfonyl isocyanate, thereby producing a third liquid medium comprising (thiophene-2-carbonyl)sulfamoyl chloride in the form of a substantially homogeneous solution or a solid suspension in a liquid organic phase comprising dibutyl ether, wherein the chlorosulfonyl isocyanate is present in the second liquid medium in molar excess relative to thiophene in the first liquid medium;

adding at least a portion of the third liquid medium to an aqueous medium comprising hydrochloric acid or sulfuric acid, thereby producing a fourth liquid medium comprising 2-thiophenecarboxylic acid dissolved in an organic phase comprising dibutyl ether; and reacting at least a portion of the 2-thiophenecarboxylic acid present in the fourth liquid medium with thionyl chloride, thereby producing a reaction medium comprising 2-thiophenecarbonyl chloride.

Embodiment 52 is a process for preparing 2-thiophenecarbonyl chloride, the process comprising:

mixing a first liquid medium comprising thiophene dissolved in dibutyl ether and a second liquid medium comprising chlorosulfonyl isocyanate, thereby producing a third liquid medium comprising (thiophene-2-carbonyl)sulfamoyl chloride in the form of a substantially homogeneous solution or a solid suspension in a liquid organic phase comprising dibutyl ether, wherein the chlorosulfonyl isocyanate is present in the second liquid medium in molar excess relative to thiophene in the first liquid medium;

adding at least a portion of the third liquid medium to an aqueous medium comprising sodium hydroxide or potassium hydroxide, thereby producing a fourth liquid medium comprising a salt form of 2-thiophenecarboxylic acid in an organic phase comprising dibutyl ether; neutralizing at least a portion of the fourth liquid medium to a fifth liquid medium comprising 2-thiophenecarboxylic acid dissolved in an organic phase comprising dibutyl ether; and reacting at least a portion of the 2-thiophenecarboxylic acid present in the fifth liquid medium with thionyl chloride, thereby producing a reaction medium comprising 2-thiophenecarbonyl chloride.

Embodiment 53 is a process for preparing 2-thiophenecarbonyl chloride, the process comprising:

mixing a first liquid medium comprising thiophene dissolved in dibutyl ether and a second liquid medium comprising chlorosulfonyl isocyanate, thereby producing a third liquid medium comprising (thiophene-2-carbonyl)sulfamoyl chloride in the form of a substantially homogeneous solution or a solid suspension in a liquid organic phase comprising dibutyl ether, wherein the chlorosulfonyl isocyanate is present in the second liquid medium in molar excess relative to thiophene in the first liquid medium;

adding at least a portion of the third liquid medium to an aqueous medium comprising water, thereby producing a fourth liquid medium comprising 2-thiophenecarboxamide; contacting at least a portion of the forth liquid medium in the presence of a strong acid or a strong base, thereby producing a fifth liquid medium of 2-thiophenecarboxylic acid in an organic phase comprising dibutyl ether; and reacting at least a portion of the 2-thiophenecarboxylic acid present in the fifth liquid medium with thionyl chloride, thereby producing a reaction medium comprising 2-thiophenecarbonyl chloride.

Embodiment 54 is the process of any one of embodiments 51 to 53 wherein the reaction is initiated by adding the first liquid medium comprising thiophene to the second liquid medium comprising chlorosulfonyl isocyanate.

Embodiment 55 is the process of any one of embodiments 51 to 53 wherein the reaction is initiated by adding the second liquid medium comprising chlorosulfonyl isocyanate to the first liquid medium comprising thiophene.

Embodiment 56 is a process for preparing a 3,5-disubstituted 1,2,4-oxadiazole of Formula (I) or a salt thereof,

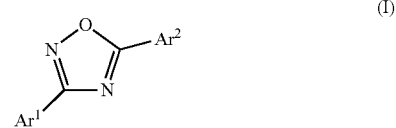

wherein $Ar^1$ is selected from the group consisting of phenyl, pyridyl, pyrazyl, oxazolyl or isoxazolyl, each of which can be optionally independently substituted with one or more substituents selected from the group consisting of halogen, $CF_3$, $CH_3$, $OCF_3$, $OCH_3$, CN and C(H)O, and $Ar^2$ is thienyl, which can be optionally independently substituted with one or more substituents selected from the group consisting of fluorine, chlorine, $CH_3$, and $OCF_3$, the process comprising reacting an N-hydroxyamidine of Formula (II), or a tautomeric form thereof,

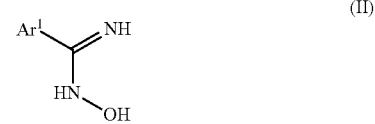

with 2-thiophenecarbonyl chloride that is prepared by a process as set forth in any one of embodiments 1 to 55.

Embodiment 57 is a process for preparing a 3,5-disubstituted 1,2,4-oxadiazole of Formula (I) or a salt thereof,

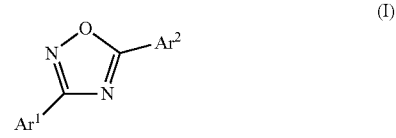

the process comprising adding a first liquid medium comprising thiophene dissolved in dibutyl ether to a second liquid medium comprising chlorosulfonyl isocyanate, thereby producing a third liquid medium comprising (thiophene-2-carbonyl)sulfamoyl chloride in the form of a substantially homogeneous solution or a solid suspension in a liquid organic phase comprising dibutyl ether, wherein the chlorosulfonyl isocyanate is present in the second liquid medium in molar excess relative to thiophene in the first liquid medium;

adding at least a portion of the third liquid medium to an aqueous medium comprising a strong acid or a strong base, thereby producing a fourth liquid medium comprising 2-thiophenecarboxylic acid dissolved in an organic phase comprising dibutyl ether; reacting at least a portion of the 2-thiophenecarboxylic acid present in the fourth liquid medium with thionyl chloride, thereby producing a reaction medium comprising 2-thiophenecarbonyl chloride; and reacting at least a portion of the 2-thiophenecarbonyl chloride obtained in the fourth liquid reaction medium with an N-hydroxyamidine of Formula (II), or a tautomeric form thereof,

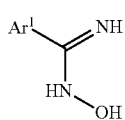

(II)

wherein $Ar^1$ is selected from the group consisting of phenyl, pyridyl, pyrazyl, oxazolyl or isoxazolyl, each of which can be optionally independently substituted with one or more substituents selected from the group consisting of halogen, $CF_3$, $CH_3$, $OCF_3$, $OCH_3$, CN and C(H)O, and $Ar^2$ is thienyl, which can be optionally independently substituted with one or more substituents selected from the group consisting of fluorine, chlorine, $CH_3$, and $OCF_3$.

Embodiment 58 is the process of embodiment 56 or 57 wherein the 3,5-disubstituted-1,2,4-oxadiazole of Formula (I) is 3-phenyl-5-(2-thienyl)-1,2,4-oxadiazole, or a salt thereof.

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the disclosure are achieved and other advantageous results attained.

As various changes could be made in the above products and methods without departing from the scope of the disclosure, it is intended that all matter contained in the above description shall be interpreted as illustrative and not in a limiting sense.

What is claimed is:

1. A process for preparing 2-thiophenecarbonyl chloride, the process comprising:
    reacting thiophene with chlorosulfonyl isocyanate in a reaction medium comprising an organic solvent, thereby producing (thiophene-2-carbonyl)sulfamoyl chloride,
    wherein the reaction is initiated by mixing the thiophene and the chlorosulfonyl isocyanate,
    and wherein the chlorosulfonyl isocyanate is present in molar excess relative to thiophene,
    hydrolyzing the (thiophene-2-carbonyl)sulfamoyl chloride to produce 2-thiophenecarboxylic acid, and
    chlorinating the 2-thiophenecarboxylic acid to produce 2-thiophenecarbonyl chloride.

2. The process of claim 1 wherein the organic solvent comprises a compound selected from the group consisting of $C_1$-$C_{10}$ alkane solvents, $C_1$-$C_{10}$ halogenated alkane solvents, $C_1$-$C_{10}$ alkylbenzenes, halogenated aromatic solvents, and dialkyl ether solvents of the general formula R—O—R', wherein R and R' are each independently selected from $C_1$-$C_6$ alkyl.

3. The process of claim 1 wherein the organic solvent comprises a compound of the formula R—O—R' wherein R is selected from $C_4$-$C_6$ cycloalkyl and R' is methyl.

4. The process of claim 1 wherein the organic solvent comprises a compound of the formula R—O—R' wherein R and R' are each $C_3$-$C_6$ alkyl.

5. A process for preparing 2-thiophenecarbonyl chloride, the process comprising:
    reacting thiophene with chlorosulfonyl isocyanate in a reaction medium comprising an organic solvent comprising dibutyl ether, thereby producing (thiophene-2-carbonyl)sulfamoyl chloride,
    hydrolyzing the (thiophene-2-carbonyl)sulfamoyl chloride to produce 2-thiophenecarboxylic acid, and
    chlorinating the 2-thiophenecarboxylic acid to produce 2-thiophenecarbonyl chloride.

6. The process of claim 1 wherein the reaction is initiated by adding the thiophene to the chlorosulfonyl isocyanate.

7. The process of claim 1 wherein the reaction is initiated by adding the chlorosulfonyl isocyanate to the thiophene.

8. The process of claim 1 wherein the hydrolysis reaction is initiated by adding the (thiophene-2-carbonyl)sulfamoyl chloride to an aqueous medium comprising a strong acid,
    and wherein the (thiophene-2-carbonyl)sulfamoyl chloride is present in the form of a substantially homogenous solution, in the form of an isolated solid, or in the form of a solid suspension in a liquid organic phase comprising the organic solvent.

9. The process of claim 1 wherein the hydrolysis reaction is initiated by adding the (thiophene-2-carbonyl)sulfamoyl chloride to a basic medium comprising a strong base,
    and wherein the (thiophene-2-carbonyl)sulfamoyl chloride is present in the form of a substantially homogenous solution, in the form of an isolated solid, or in the form of a solid suspension in a liquid organic phase comprising the organic solvent.

10. The process of claim 1 wherein the hydrolysis reaction medium is allowed to separate into an aqueous phase and an organic phase comprising the 2-thiophenecarboxylic acid,
    and wherein the organic phase comprising the 2-thiophenecarboxylic acid is separated from the aqueous phase.

11. The process of claim 1 wherein the 2-thiophenecarboxylic acid is dissolved in the organic solvent and reacted with the chlorinating agent to produce 2-thiophenecarbonyl chloride in a liquid medium.

12. The process of claim 11 wherein the chlorination reaction is initiated by adding a first liquid medium comprising thionyl chloride to a second liquid medium comprising the 2-thiophenecarboxylic acid.

13. The process of claim 12 wherein the chlorination reaction is carried out in the presence of a catalyst that promotes formation of 2-thiophenecarbonyl chloride.

14. The process of claim 1, comprising:
    mixing a first liquid medium comprising the thiophene dissolved in dibutyl ether and a second liquid medium comprising the chlorosulfonyl isocyanate, thereby producing a third liquid medium comprising the (thiophene-2-carbonyl)sulfamoyl chloride in the form of a substantially homogeneous solution or a solid suspension in a liquid organic phase comprising dibutyl ether;

adding at least a portion of the third liquid medium to an aqueous medium comprising hydrochloric acid or sulfuric acid, thereby producing a fourth liquid medium comprising 2-thiophenecarboxylic acid dissolved in an organic phase comprising dibutyl ether; and reacting at least a portion of the 2-thiophenecarboxylic acid present in the fourth liquid medium with thionyl chloride, thereby producing a reaction medium comprising 2-thiophenecarbonyl chloride.

15. The process of claim 1, comprising:

mixing a first liquid medium comprising the thiophene dissolved in dibutyl ether and a second liquid medium comprising the chlorosulfonyl isocyanate, thereby producing a third liquid medium comprising the (thiophene-2-carbonyl)sulfamoyl chloride in the form of a substantially homogeneous solution or a solid suspension in a liquid organic phase comprising dibutyl ether;

adding at least a portion of the third liquid medium to an aqueous medium comprising sodium hydroxide or potassium hydroxide, thereby producing a fourth liquid medium comprising a salt form of 2-thiophenecarboxylic acid in an organic phase comprising dibutyl ether;

neutralizing at least a portion of the fourth liquid medium to a fifth liquid medium comprising 2-thiophenecarboxylic acid dissolved in an organic phase comprising dibutyl ether; and reacting at least a portion of the 2-thiophenecarboxylic acid present in the fifth liquid medium with thionyl chloride, thereby producing a reaction medium comprising 2-thiophenecarbonyl chloride.

16. The process of claim 1, comprising:

mixing a first liquid medium comprising the thiophene dissolved in dibutyl ether and a second liquid medium comprising the chlorosulfonyl isocyanate, thereby producing a third liquid medium comprising the (thiophene-2-carbonyl)sulfamoyl chloride in the form of a substantially homogeneous solution or a solid suspension in a liquid organic phase comprising dibutyl ether;

adding at least a portion of the third liquid medium to an aqueous medium comprising water, thereby producing a fourth liquid medium comprising 2-thiophenecarboxamide;

contacting at least a portion of the fourth liquid medium in the presence of a strong acid or a strong base, thereby producing a fifth liquid medium of 2-thiophenecarboxylic acid in an organic phase comprising dibutyl ether; and reacting at least a portion of the 2-thiophenecarboxylic acid present in the fifth liquid medium with thionyl chloride, thereby producing a reaction medium comprising 2-thiophenecarbonyl chloride.

17. A process for preparing a 3,5-disubstituted 1,2,4-oxadiazole of Formula (I) or a salt thereof,

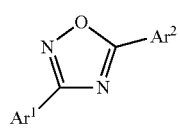

wherein $Ar^1$ is selected from the group consisting of phenyl, pyridyl, pyrazyl, oxazolyl or isoxazolyl, each of which can be optionally independently substituted with one or more substituents selected from the group consisting of halogen, $CF_3$, $CH_3$, $OCF_3$, $OCH_3$, CN and C(H)O, and $Ar^2$ is thienyl, which can be optionally independently substituted with one or more substituents selected from the group consisting of fluorine, chlorine, $CH_3$, and $OCF_3$, the process comprising reacting an N-hydroxyamidine of Formula (II), or a tautomeric form thereof,

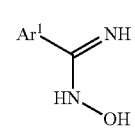

with 2-thiophenecarbonyl chloride that is prepared by the process as set forth in claim 1.

18. A process for preparing a 3,5-disubstituted 1,2,4-oxadiazole of Formula (I) or a salt thereof,

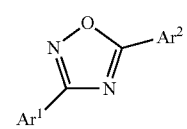

the process comprising adding a first liquid medium comprising thiophene dissolved in dibutyl ether to a second liquid medium comprising chlorosulfonyl isocyanate, thereby producing a third liquid medium comprising (thiophene-2-carbonyl)sulfamoyl chloride in the form of a substantially homogeneous solution or a solid suspension in a liquid organic phase comprising dibutyl ether, wherein the chlorosulfonyl isocyanate is present in the second liquid medium in molar excess relative to thiophene in the first liquid medium;

adding at least a portion of the third liquid medium to an aqueous medium comprising a strong acid or a strong base, thereby producing a fourth liquid medium comprising 2-thiophenecarboxylic acid dissolved in an organic phase comprising dibutyl ether;

reacting at least a portion of the 2-thiophenecarboxylic acid present in the fourth liquid medium with thionyl chloride, thereby producing a reaction medium comprising 2-thiophenecarbonyl chloride;

and reacting at least a portion of the 2-thiophenecarbonyl chloride obtained in the fourth liquid reaction medium with an N-hydroxyamidine of Formula (II), or a tautomeric form thereof,

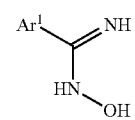

wherein $Ar^1$ is selected from the group consisting of phenyl, pyridyl, pyrazyl, oxazolyl or isoxazolyl, each of which can be optionally independently substituted with one or more substituents selected from the group consisting of halogen, $CF_3$, $CH_3$, $OCF_3$, $OCH_3$, CN and C(H)O, and $Ar^2$ is thienyl, which can be optionally independently substituted with one or more substituents selected from the group consisting of fluorine, chlorine, $CH_3$, and $OCF_3$.

19. The process of claim 5, wherein the reaction is initiated by adding the thiophene to the chlorosulfonyl isocyanate.

* * * * *

UNITED STATES PATENT AND TRADEMARK OFFICE
CERTIFICATE OF CORRECTION

PATENT NO. : 10,239,857 B2
APPLICATION NO. : 15/563008
DATED : March 26, 2019
INVENTOR(S) : Daniel P. Walker and William H. Miller Page 1 of 1

It is certified that error appears in the above-identified patent and that said Letters Patent is hereby corrected as shown below:

In the Claims

Column 23, Line 67 to Column 24, Line 3, Claim 17: "$CF_3$, $CH_3$, $OCF_3$, $OCH_3$, CN and C(H)O, and $Ar^2$ is thienyl, which can be optionally independently substituted with one or more substituents selected from the group consisting of fluorine, chlorine, $CH_3$, and $OCF_3$," Should read -- $CF_3$, $CH_3$, $OCF_3$, $OCH_3$, CN and C(H)O, and $Ar^2$ is thienyl, --

Column 24, Lines 64-67, Claim 18: "$CF_3$, $CH_3$, $OCF_3$, $OCH_3$, CN and C(H)O, and $Ar^2$ is thienyl, which can be optionally independently substituted with one or more substituents selected from the group consisting of fluorine, chlorine, $CH_3$, and $OCF_3$." Should read -- $CF_3$, $CH_3$, $OCF_3$, $OCH_3$, CN and C(H)O, and $Ar^2$ is thienyl. --

Signed and Sealed this
Fifth Day of May, 2020

Andrei Iancu
*Director of the United States Patent and Trademark Office*